United States Patent [19]

Barnes

[11] 4,315,157
[45] Feb. 9, 1982

[54] MULTIPLE BEAM COMPUTED TOMOGRAPHY (CT) SCANNER

[75] Inventor: Gary T. Barnes, Birmingham, Ala.

[73] Assignee: The University of Alabama in Birmingham, Birmingham, Ala.

[21] Appl. No.: 145,820

[22] Filed: May 1, 1980

[51] Int. Cl.³ .............................................. A61B 6/00
[52] U.S. Cl. ............................................... 250/445 T
[58] Field of Search ................................... 250/445 T

[56] References Cited

U.S. PATENT DOCUMENTS 4,132,895  1/1979  Froggart ........................ 250/445 T
4,220,863  9/1980  McBride et al. ................ 250/445 T Primary Examiner—Alfred E. Smith
Assistant Examiner—T. N. Grigsby
Attorney, Agent, or Firm—Oblon, Fisher, Spivak, McClelland & Maier

[57] ABSTRACT

A multiple beam computed tomography (CT) scanner formed of plural interspaced groups of small, densely packed radiation detectors provided in a stationary ring around a body. The ring defines the cross-sectional slice of the body which is scanned by moving an X-ray source in a circle having a smaller radius and the same plane and center as that of the detector ring. A rotatably mounted collimator having a plurality of beam defining apertures is positioned between the X-ray source and patient. The collimator defines a plurality of fan-shaped X-ray beams that strike the detectors after passing through the patient and eliminates radiation from impinging on the patient that would pass through and strike the dead spaces between detector groups. The X-ray source and collimator rotate synchronously maintaining the registration between any given X-ray beam and detector group while the area of interest for the given detector group is scanned by the X-ray beam.

11 Claims, 8 Drawing Figures

MULTIPLE BEAM COMPUTED TOMOGRAPHY (CT) SCANNER

BACKGROUND OF THE INVENTION

1. Field of the Invention

This invention relates to the field of radiography, and more particularly to a fourth generation Computed Tomography (CT) Scanner having an optimized scanner geometry.

2. Description of the Prior Art

Computed tomography processes are a modern technique developed to provide a non-invasive means for revealing internal organs and tissues of a human body in cross-section for the purpose of diagnosing the condition of the particular cross-section of the body being examined. Basically, computed tomographic techniques utilize a series of x-ray projections or views made from different angles, which are taken axially through a "slice" or thin cross-sectional area of a patient. The X-rays generated by a radiographic source, or in some instances Gamma Rays from a radioactive source, are transmitted transversely through a section of the patient's anatomy and are detected by a high-efficiency radiation detectors. Each projection or view of the cross-sectional "slice" consists of a series of ray paths or samples through the section with differences in the ray samples arising from attenuation differences in the slice or differences in path length through the slice. The different angular projections of the subject with each angular projection, comprised of a series of discrete ray samples provides the input by which x-ray or gamma ray attenuation coefficients can be calculated in a computer and the image of the cross-section of the patient's anatomical variations reconstructed. Thus, a computed tomography scanner obtains, by mathematical reconstruction, a transverse sectional image from transmitted radiation projection data, as is well known.

In the past several years, advances in computed tomography techniques have resulted in several generations of scanners. In the first scanner commercially marketed, the series of ray samples comprising a given projection was obtained by a translational movement of the x-ray source and a detector. The source and detector were stopped and rotated and the sequence repeated to obtain the different angular projections. In a 2nd generation scanner the data gathering process is much the same except several detectors were employed allowing for greater angular increments per rotation and fewer rotations resulting in shorter scan times. In 3rd generation geometries the x-ray source and detector array pivot around a common point in a single rotational movement and the x-ray beam sequentially pulsed giving rise to the different angular projections; while in 4th generation geometries, the different projections of the slice arise from the ring of stationary detectors placed around the slice with each detector taking sequential samples as the x-ray source rotates around the slice giving rise to a different angular projection. Compared to the 1st generation scanner, the 2nd, 3rd and 4th generation geometries detect a greater portion of the X-rays produced allowing for shorter scan times. The ease of the pure and continuous rotational movement upon the initiation of a scan of the 3rd and 4th generation machines compared to the start/stop motions associated with the earlier designs results in their being the current geometries marketed by most manufacturers.

In 3rd generation geometries the distance between samples in a projection is the detector-to-detector spacing which is coarse and limits the scanner's spatial resolution. In 1st, 2nd and 4th generation geometries the projections can be finely sampled and the basic limitation is the size of the detector aperture. Other factors which may limit the spatial resolution of a CT scanner are the cutoff frequency, $f_c$, of the reconstruction algorithm or the Nyquist frequency, $f_p$, of the image display consisting of square pixels of finite size. The algorithm cutoff frequency $f_c$ is usually (but not always) matched to the fundamental limitation of the scanner which is dictated by the smallest value of either the sampling Nyquist frequency ($f_s$), the pixel display Nyquist frequency ($f_p$), or the detector aperture cutoff frequency ($f_a$).

Currently, detector apertures in 4th generation geometries are approximately four mm and anatomical detail much smaller than this is therefore not sharply defined. While the detector apertures can be stopped down, or made smaller to improve the scanner's resolution, when this is done a larger percentage of the X-rays emerging from the patient strike dead space between the detectors and are wasted, thereby reducing the x-ray dose efficiency discussed in more detail hereinafter. Obviously, those X-rays which strike detector dead space contribute no information to the resultant image, and their loss results in increased radiation dose to the patient.

At present, the major component of a CT Scanner's manufacturing cost is associated with the detectors, detector electronics, and computer processing system which in turn is dependent upon the number of detectors employed. Thus, when detector size is reduced to improve resolution and system performance, a greater number of detectors is required and the cost of the overall CT system is concomitantly increased such that a clear tradeoff between cost and resolution is evidenced by the present state of the art. In order to stay within reasonable commercial constraints, current 3rd and 4th generation scanners typically have between 500 and 1,200 detectors.

The concept of prepatient collimation to confine the x-ray beam to the region of interest to reduce the deleterious effects of large beams of radiation has been widely used in the medical x-ray industry since the turn of the century. It is currently employed in CT scanners to define the slice thickness and detector assemblies. Additional prepatient collimation designed to reduce the percentage of radiation striking the dead spaces between detectors has been introduced for 2nd generation geometries and marketed by EMI and Elscint. However, due to the geometrical unsharpness of the collimator at the detectors resulting from the finite size of the focal spot, such collimation schemes do not result in geometrical efficiencies of much greater than 65%. Ohio Nuclear also announced a 4th generation CT scanner, the 2020 Δ-Scanner, which employed prepatient collimation. Their design consisted of a stationary ring of 720 4 mm detectors separated by 4 mm of dead spaces and the objective was to eliminate radiation from striking the 4 mm dead spaces. However, this design was dropped due to the finite size of the focal spot and the x-ray optics of the geometry making it impossible to confine the x-ray beam with prepatient collimation to the 4 mm detectors without a significant amount of radiation striking the dead spaces and also resulting in a significant loss in the x-ray flux striking the detectors.

Another prior art CT Scanner, the 7000 series by EMI Ltd., a variant 4th generation geometry consisting of a Nutating ® rather than stationary array of 1,112 batch produced solid state detectors arranged as a small ring that wobbles as the x-ray source rotates around the patient, in which the detectors at 180° from the x-ray source are translated in the opposite direction allowing the x-ray beam to strike the former. The circle defined by the rotation of the x-ray source is larger than that of the detector ring. Advantageously, the EMI 7000 CT Scanner enjoys improved system resolution as a result of the smaller detectors employed, and also reduced dead space due to close packing of the detectors.

The motivation for the design lies in the fact that fewer detectors are required than would be in the larger ring diameter of a conventional 4th generation design to achieve the same resolution. Nevertheless, while the EMI 7000 CT Scanner realizes improved system performance, the improvement is achieved at high cost due to the complicated mechanics of the Nutating ® detector ring implementation. Furthermore, since the EMI 7000 Series approach employs a small detector ring, further advances in system performance are very much limited to detector technology, and more specifically, detector aperture size. Then, even if additional smaller detectors are used, the above-described tradeoff must nevertheless play the dominant role in arriving at a final system design.

Yet another CT Scanner under consideration by Pfizer involves the possibility of employing a conventional 4th generation design consisting of a stationary detector array comprised of a large number, as many as 2,400, small detectors essentially equivalent at least in their size and x-ray detection efficiency to those currently being used in the EMI 7000 Scanner. Once again, however, arbitrary increase in the number of detectors significantly complicates the detector electronics and related computer processing system, greatly increasing the cost of the total system.

Examples of additional prior art CT Scanners are found in U.S. Pat. Nos. 4,123,659 to Oliver, 4,101,768 to Lill, 4,097,747 to Kowalski, 4,097,744 to LeMay, 4,096,391 to Barnes, 4,096,389 to Ashe, 4,091,289 to LeMay, 4,075,491 to Boyd, 4,066,901 to Seppi, 4,048,505 to Hounsfield, 4,031,395 to LeMay, and 3,684,886 to Muehllegner.

SUMMARY OF THE INVENTION

Accordingly, it is one object of this invention to provide a novel Computer Tomography (CT) Scanner exhibiting improved contrast sensitivity and spatial resolution.

Another object of this invention is to provide a novel CT Scanner in which x-ray dose efficiency to the patient is maximized.

Yet another object of this invention is to provide a novel CT Scanner capable of producing high resolution diagnostic data with a minimum of detectors and data acquisition electronics.

These and other objects are achieved according to the invention by providing a new and improved CT Scanner including a series of stationary detector groups symmetrically arranged around a detector ring. Typically, depending upon the system requirements, the scanner has 25 to 99 groups of detectors with each detector group consisting of 10 to 60 detectors. The size of each detector aperture is typically 2 mm or less. In order to eliminate unnecessary patient exposure to x-ray radiation, a prepatient x-ray collimator is disposed between the x-ray source and the patient to eliminate patient exposure to X-rays in sectors between detector groups. During a scan, in one embodiment, the collimator synchronously rotates around the x-ray tube focal spot such that the collimator apertures maintain alignment with the detector groups. In another embodiment the collimator synchronously rotates around the center of the patient circle to achieve the requisite prepatient x-ray collimation. In either embodiment while the x-ray tube rotates clockwise about the center of the detector ring through an angle $\theta$, the collimator moves counterclockwise through a corresponding angle $\phi$ relative to the focal spot where the movement of the x-ray focal spot and the collimator is governed by the transcendental equation $$R \cdot \sin(\theta - \phi) = r \cdot \sin \phi \qquad (1)$$

where r and R are the radii of circles defined by the locus of the X-ray tube focal spot and the detector ring, respectively. The size of the collimator is such that it is positioned relatively close to the patient, which along with the employment of a small focal spot x-ray tube and the fact that the collimator apertures define a beam of about 2–10 cm (at the detector ring) minimizes penumbra problems.

The computed tomography (CT) scanner of the invention realizes improved image quality and resolution for cross-sectional slices of a patient body for a given radiation dose. The improved spatial resolution and image quality obtained with the invention is primarily a result of the small detectors employed, while the use of groups of detectors rather than a continuous ring of detectors allows this improvement to be realized for a modest manufacturing cost. The prepatient collimator eliminates X-rays from impinging on the patient that would strike the inactive areas between detector groups, thereby allowing virtually all the primary radiation penetrating the patient to be detected and minimizing the radiation dose to the patient.

Another factor improving the image quality obtained with the invention is that the percentage of scatter detected is less than that of a more conventional design. This results because smaller X-ray beams and a smaller active detector area are employed.

BRIEF DESCRIPTION OF THE DRAWINGS

A more complete appreciation of the invention and many of the attendant advantages thereof will be readily obtained as the same becomes better understood by reference to the following description when considered in connection with the accompanying drawings, wherein.

DETAILED DESCRIPTION OF THE PREFERRED EMBODIMENTS

Figure 1:
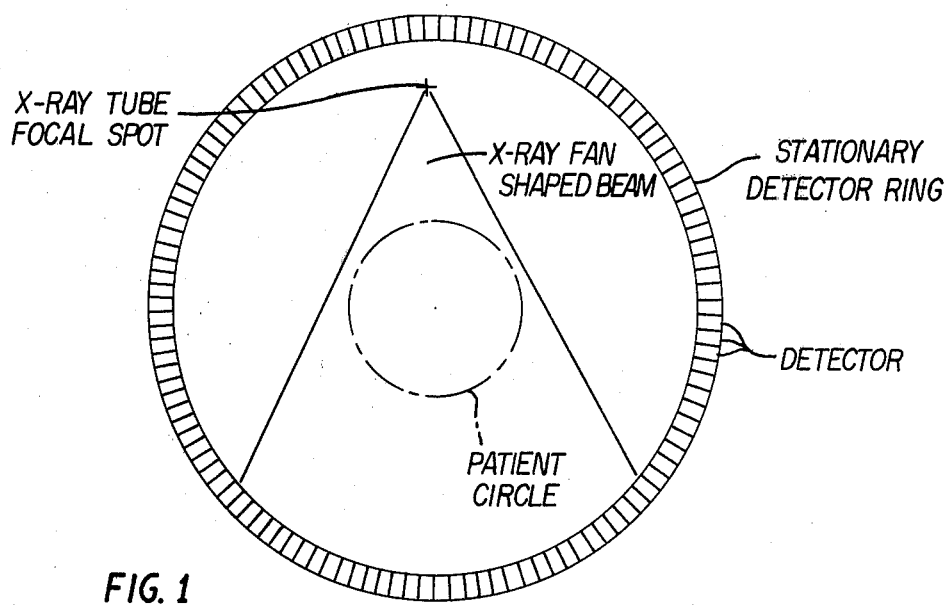
FIG. 1 is a schematic end elevational view illustrating the geometry of a conventional fourth generation CT Scanner.
Figure 2:
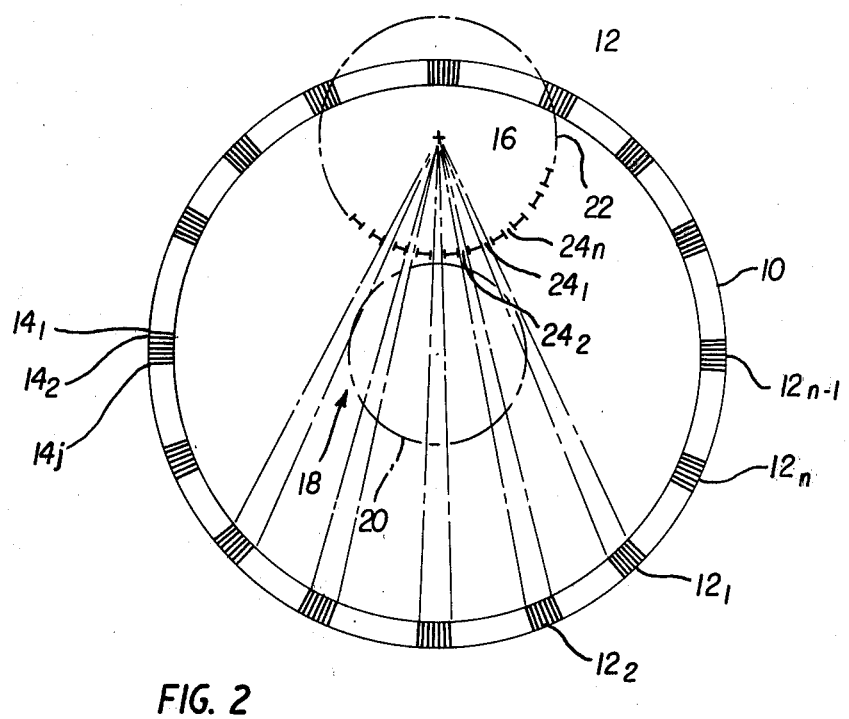
FIG. 2 is an end elevational view illustrating the geometry of the multiple beam fourth generation CT Scanner according to the invention.

Referring now to the drawings, wherein like reference numerals designate identical or corresponding parts throughout the several views, and more particularly to FIG. 2 thereof, there is seen schematically the multiple beam fourth generation CT scanner according to the invention which includes a stationary detector ring 10 formed of plural groups $12_1$ through $12_n$ of individual detectors, with the detectors of each group designated by the reference numerals $14_1$ through $14_j$. An X-ray source having a schematically illustrated focal spot 16 is disposed within the detector ring and irradiates with X-ray radiation a cross-sectional slice of a patient 18, the cross-sectional slice schematically illustrated in FIG. 2 as the patient circle 20. Disposed between the X-ray source focal spot 16 and the patient circle 20 is a prepatient collimator 22 having a plurality of collimator apertures $24_1$ through $24_n$, with each collimator aperture $24_n$ corresponding to a respective detector group $12_n$.

Figure 3:
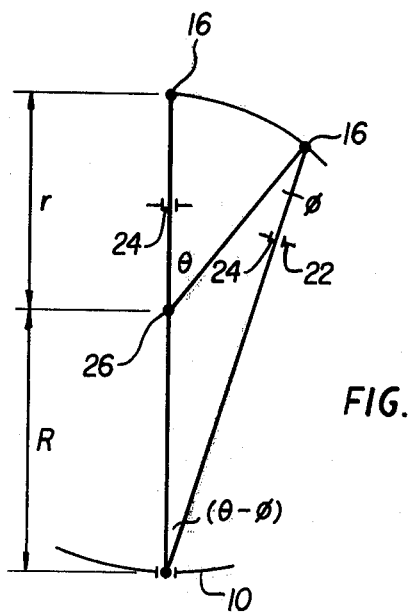
FIG. 3 is a schematic diagram illustrating the angular relationships between the X-ray focal spot, collimator, patient circle, and detector ring of the CT Scanner according to the invention.

As shown in FIG. 3, during a scan, the locus of the X-ray source focal spot 16 defines a circle having a smaller diameter than that of the detector ring. If the focal spot 16 moves clockwise through an angle $\theta$, the collimator 22 is rotated counter-clockwise about the X-ray tube focal spot 16 so that the focal spot 16 and a given collimator aperture $24_n$ and a corresponding detector group $12_n$ remain aligned. The angular relationships are depicted in FIG. 3, where $\phi$ is the counter-clockwise rotation of the collimator 22 about the focal spot, r is the radius of the circular focal spot locus and R is the radius of the detector ring. Assuming that the focal spot 16 and a given collimator aperture $24_n$ and detector group $12_n$ are aligned initially ($\theta = \phi = 0°$), they will also be aligned subsequently when $\theta$ and $\phi$ are related to the transcendental equation $$R \cdot \sin(\theta - \phi) = r \cdot \sin \phi \qquad (1)$$

Generally, each collimator aperture 24 is sufficiently large so that regardless of the collimator rotation angle $\phi$, the primary X-rays reaching the patient 18 and which are defined by the collimator aperture 24 impinge completely over the entire respective detector group 12 with little overlap, thereby maximizing the radiation dose efficiency to the patient. It is, however, noted that between the initial location and the position given by the angles defined by equation (2), the collimator aperture will be slightly misaligned with the focal spot and the detector group. However, for practical situations (i.e., $\theta - \phi = 10°$; r = 66 cm; and R = r·$\sqrt{3}$) and detector groups having 3.5 cm of arc, the misalignment is extremely small and results in a negligibly small loss of primary X-rays defined by the collimator. A greater loss of primary X-rays results from the unsharpness at the detector group. However, for a 40 cm focal spot-to-collimator distance, a 0.4 mm focal spot, and the geometry defined above, the total loss of primary X-rays is approximately 5%.

Nevertheless, according to the multiple beam CT Scanner of the invention employing a prepatient collimator, the prepatient collimation itself is advantageous since the detector groups are on the order of centimeters and large compared to the collimator unsharpness. That is, whenever the dimension, L, to be defined at the detector ring by a prepatient collimating diaphragm is larger than the projected unsharpness of the diaphragm edge $U_g$, then prepatient collimation will result in a significant improvement in the geometrical efficiency with little loss in detected X-ray flux for a given technique. Expressed mathematically, the condition is $$L > U_g \qquad (2)$$

wherefore focal spot size a, and magnification m, $U_g$ is given by $$U_g = a \cdot (m - 1) \qquad (3)$$

where the magnification, m, is defined as the distance from the focal spot to the detector divided by the distance from the focal spot to the collimator.

Figure 4:
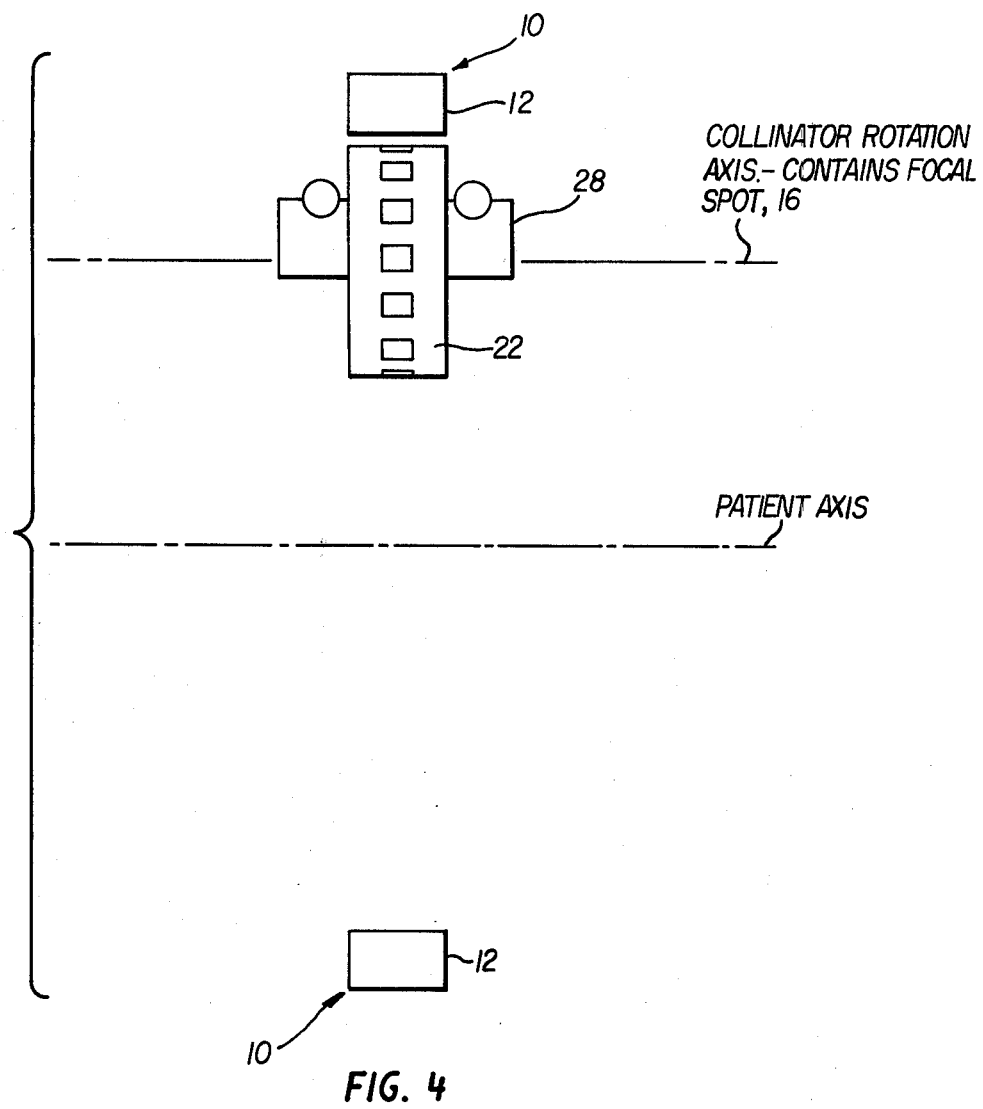
FIG. 4 is a schematic side elevational view of one embodiment of the multiple beam CT Scanner according to the invention employing a collimator rotating about the X-ray source focal spot.

For scanners in which the focal spot lies closer to the patient circle than to the detector ring or midway between prepatient collimation close to the patient circle 20 can be achieved by the configuration illustrated in FIG. 4. In FIG. 4, the collimator 22 of the invention is shown rotating in the manner shown in FIG. 2 about an axis that passes through the X-ray tube focal spot 16 and is parallel to the long dimension of the detectors 12. The collimator 22 has a cylindrical shape with the collimating apertures 24 being rectangles which are slightly larger than the size of the detector groups 12 projected back to the collimator 22. The slightly larger collimator aperture size allows for the slight misalignment discussed previously that occurs during a scan between the focal spot 16 and any given detector group 12.

Figure 5:
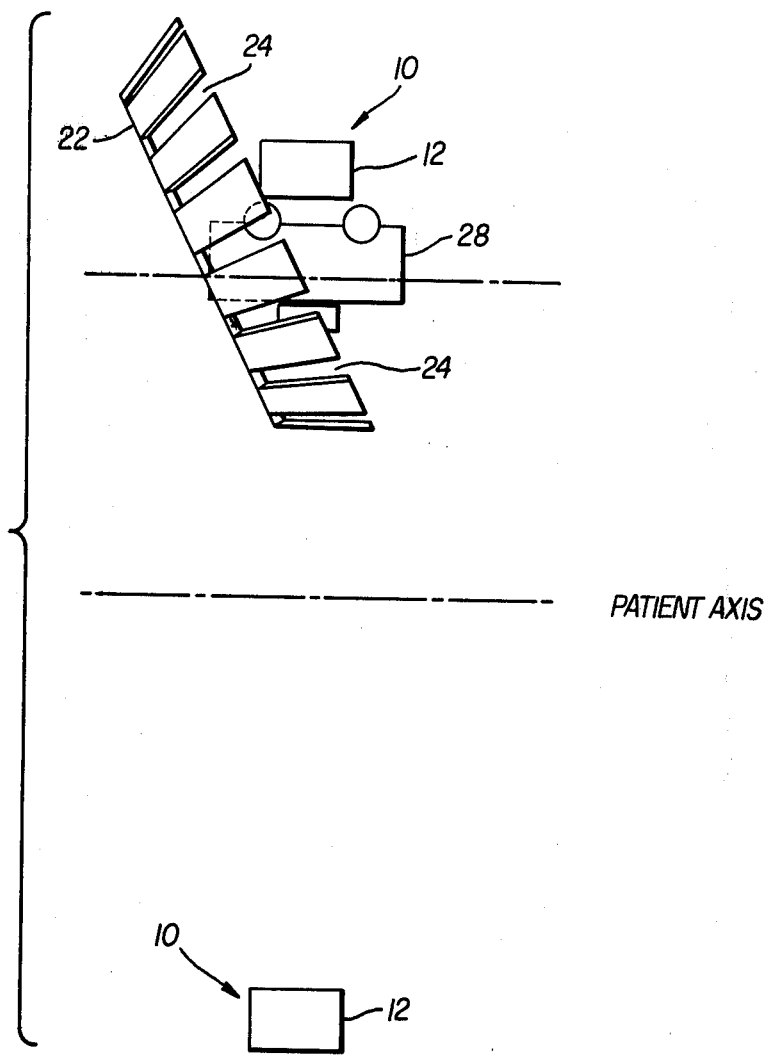
FIG. 5 is a schematic side view of another embodiment of the multiple beam CT Scanner employing a collimator having a tilted frustum design.
Figure 6:
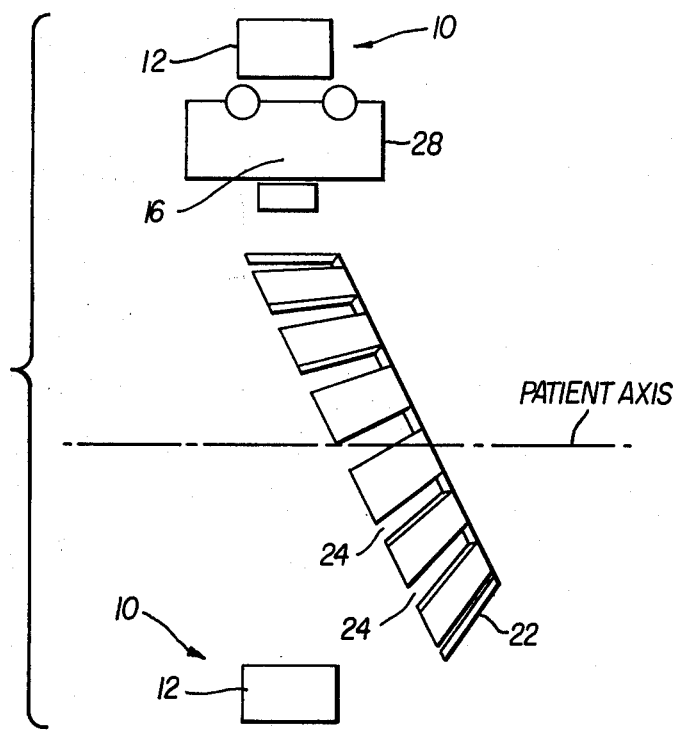
FIG. 6 is a schematic side elevational view of another embodiment of the multiple beam CT Scanner according to the invention employing a collimator which rotates about the center of the patient circle.

In order to achieve prepatient collimation close to the patient when the focal spot 16 is positioned closer to the detector ring 10 than to the patient circle 20, the collimator 22 of the invention in such a configuration employs a tilted frustum design as illustrated in FIGS. 5 and 6. In FIG. 5, the tilted frustum collimator 22 of the invention is shown rotating about an X-ray source 16 and the detector ring 10, in the manner shown in FIG. 3. On the other hand, in the embodiment shown in FIG. 5, the tilted frustum collimator 22 of the invention can otherwise be rotated around the center of the patient circle. In the embodiments as noted above, the goal is to locate the collimator 22 as close as possible to the patient, with the collimator aperture 24 disposed in a direct line between the X-ray source 16 and the patient 18 defining a plane perpendicular to this direct line between the X-ray source 16 and the patient 18. It has been found that the employment of an X-ray tube having a small focal spot in combination with collimator apertures defining a beam of greater than one cm reduces penumbra problems and correspondingly enhances the overall system resolution.

It should be understood that the scanner of the invention additionally employs a collimation that determines the beam slice thickness. In prior art scanners the slice thickness is variable, either continuously or in a series of discrete steps. For example, in the GE CT/T 8800 scanner one has a choice of 5 or 10 mm thick slices. In the multiple beam scanner according to the invention slice thickness collimation is not novel and is accomplished in a manner similar to that of the prior art.

Figure 7:
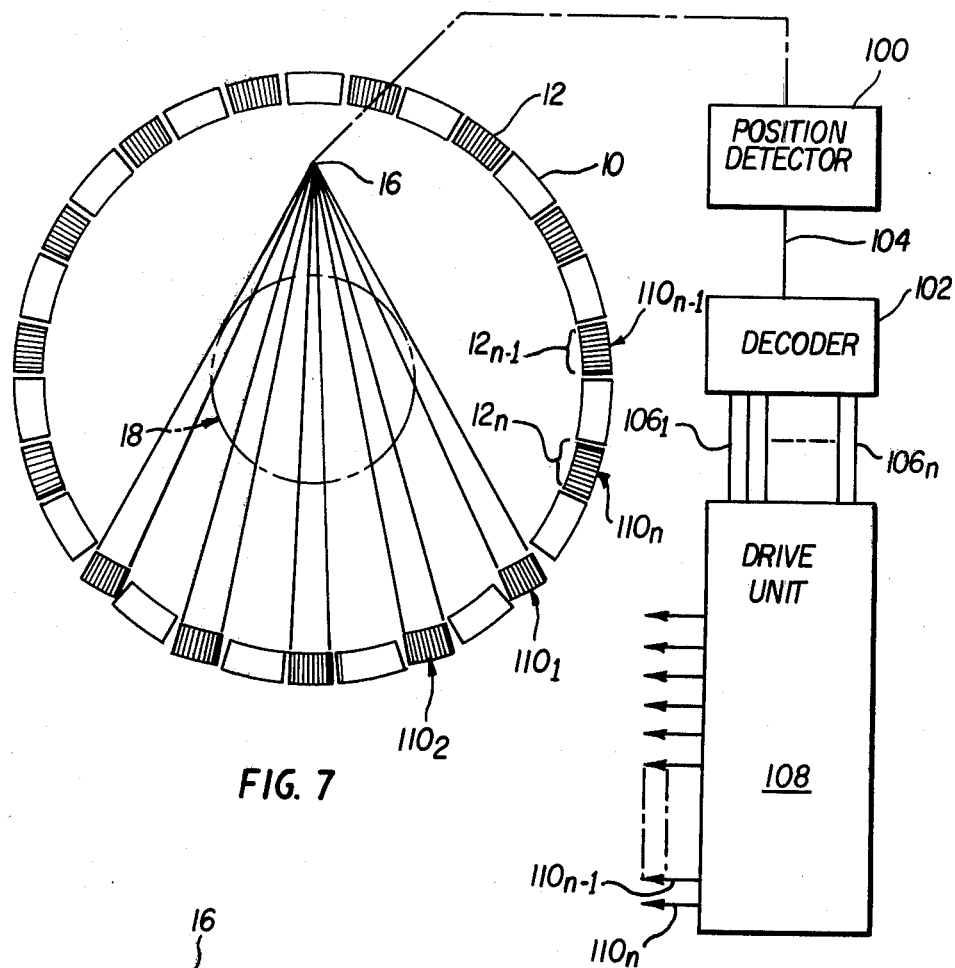
FIG. 7 is a schematic end elevational view illustrating the geometry of another embodiment of the multiple beam fourth generation CT scanner according to the invention.

In FIG. 7 is shown another embodiment of the invention in which the individual detector groups 12 track the focal spot 16 during the revolution of the focal spot 16 around the patient, such that X-ray radiation from focal spot 16 is incident at essentially a 90° angle on each detector aperture of the tracking detector groups. In FIG. 7, focal spot position is monitored by a conventional position detector 100, the output of which is applied to a conventional decoder 102. Decoder 102 converts focal spot position data 104 obtained from detector 100 into respective position tracking signals 106n which are applied to a servo drive unit 108 which outputs respective positioning drive signals $110_n$ to each of the detector groups $12_n$, to maintain tracking of the detector groups $12_n$ as the focal spot revolves around the patient.

The FIG. 7 embodiment allows the use of gas or low atomic number solid state detectors, whereas current detectors employed in 4th generation geometries necessarily have a high X-ray stopping power (i.e., a high density and atomic number).

Nextly, the theory and terminology for analyzing the performance of the CT scanner of the invention in comparison with that of prior art third and fourth generation CT scanners and the EMI 7000 series discussed above is presented.

Important parameters of CT scanner performance are dose efficiency and resolution. The dose efficiency, $\epsilon_{rad}$, is defined as the ratio of detected X-ray photons to those emerging from the patient and is equal to product of the geometrical detection efficiency, $\xi_{geo}$, and the detector's X-ray conversion efficiency $\xi_{con}$, or $$\xi_{rad} = \xi_{geo} \cdot \xi_{con} \qquad (4)$$

$\xi_{geo}$ is the ratio of the sensitive detector area to the area that X-rays emerging from the patient impinge on, and $\xi_{con}$ is the fraction of X-rays incident on the sensitive detector area that is detected.

For a given type of patient compensating filter and X-ray beam quality the patient radiation absorbed dose of a CT scanner is proportional to the number of detected photons, $N_{det}$, divided by the dose efficiency, or $$\text{Patient Dose (rads)} \sim N_{det}/\xi_{rad} \qquad (5)$$

That is, for a given number of detected X-rays patient dose is inversely related to the scanner's dose efficiency. $\xi_{rad}$, $\xi_{geo}$ and $\xi_{con}$ are tabulated in Table I for the three prior art CT scanners discussed above. The data in Table I indicates that the EMI 7000 series scanner has the best dose efficiency. The dose efficiency of the 3rd generation GE CT/T 8800 scanner is limited by the X-ray conversion efficiency of its detectors; while the dose efficiency of 4th generation Ohio Nuclear Δ-Scan 2020 is limited by its geometrical detection efficiency.

TABLE I

Geometrical, Conversion and Dose Efficiencies for Prior Art CT Scanners

| Manufacturer and Unit | Geometrical Efficiency, % | Detection Conversion Efficiency, % | Dose Efficiency, % |
|---|---|---|---|
| Ohio Nuclear Δ-Scan 2020 | 50 | 100 | 50 |
| GE CT/T 8800 | 74 | 73 | 54 |
| EMI 7000 | 78 | 90 | 70 |

As noted previously, the resolution (i.e., the highest spatial frequency that can be resolved) of a CT scanner is limited by either the sampling Nyquist frequency $f_s$, the cutoff frequency of the detector aperture $f_a$, or the Nyquist frequency of the pixel display $f_p$, with the algorithm cutoff frequency $f_c$ generally matched to the limiting factor.

For a distance d between samples (measured at the detector), the well known sampling theorem indicates that the highest spatial frequency that can be resolved is given by the sampling Nyquist frequency. Expressed at the center of the reconstructed image (i.e., the pivot point) the sampling Nyquist frequency $f_s$ is $$f_s = M/(2 \cdot d) \qquad (6)$$

where M is the geometrical magnification factor of the pivot point and is given by the X-ray source-to-detector distance divided by the X-ray source-to-pivot distance. The cutoff frequency expressed at the pivot point for a detector aperture of width w is $$f_a = M/w \qquad (7)$$

and the Nyquist frequency of the pixel display comprised of square elements of dimension p is $$f_p = 1/(2 \cdot p) \qquad (8)$$

The geometrical dimensions and associated cutoff frequencies are tabulated in Table II and III for three prior art CT scanners. As discussed previously, the factor limiting the resolution of the 4th generation Ohio Nuclear Δ-Scan 2020 is its effective detector aperture width (i.e., w/M) and its resolution can only be improved by reducing this parameter. Generally, if smaller detectors or a greater magnification is employed, either more detectors are required or a greater dead space occurs between detectors. The former would increase the cost of the system while the latter would reduce its dose efficiency.

TABLE II

Pertinent Data for Prior Art CT Scanners

| Manufacturer and Unit | Focus-to-Det. Dist. (cm) | Pivot Point Mag. | Focal spot (mm) | Detector aperture (mm) | Det. Cut-frequency (cm$^{-1}$) |
|---|---|---|---|---|---|
| Ohio Nuclear Δ-Scan 2020 | 153.1 | 2.48 | 0.6 | 4 | 6.2 |
| GE CT/T 8800 | 110.7 | 1.42 | 1.2 | 0.90 | 15.8 |
| EMI 7000 | 107.9 | 1.62 | 0.6 | 1.79 | 9.1 |

| Manufacturer and Unit | Sampling Distance (mm) | Sam.Nyquist Frequency (cm$^{-1}$) | Pixel size* (mm) | Pixel Nyquist Frequency* (cm$^{-1}$) |
|---|---|---|---|---|
| Ohio Nuclear Δ-Scan 2020 | 0.62 | 20 | 0.5 | 10 |

TABLE II-continued

| Pertinent Data for Prior Art CT Scanners | | | | |
|---|---|---|---|---|
| GE CT/T 8800 | 1.21 | 5.9 | 0.78 | 6.4 |
| EMI 7000 | 0.85 | 9.5 | 0.75 | 6.7 |

*Head scan mode, i.e., a 24 or 25 cm diameter patient circle

The factor limiting the resolution of the 3rd generation GE CT/T 8800 scanner is its sampling distance. This distance is the detector-to-detector spacing and reducing it requires that effectively smaller detectors, and therefore more detectors, be employed. The variant 4th generation EMI 7000 scanner employs more detectors (1,112) and its resolution in the head scan mode is limited by the pixel display. However, if a display incorporating smaller pixels, say −0.5 mm, is employed, the resolution would also be limited by the effective size of its detector aperture. For further analysis of the factors affecting CT scanner resolution, reference is made to Yester and Barnes, "Geometrical Limitations of Computer Tomography (CT) Scanner Resolution," Proc. Society of Photo-Optical Instrumentation Engineers (SPIE), Volume 127, 1977, pp. 296-303.

In addition to the number of X-ray photons comprising an image and the CT scanner's resolution, the information contained in the image also depends on spatial frequency response of the CT scanner over the ranges of frequencies reconstructed. This is best described employing information theory and it has been shown by other investigators that the information capacity of a CT scanner is given by $$\text{Information Capacity} = (1.44 \cdot N_{neq}/D) \cdot \int_0^{f_c} MTF_{geo}(f) \cdot df \quad (9)$$

where $N_{neq}$ is the noise equivalent number of quanta comprising the reconstructed image, D is the diameter of the reconstructed image, $MTF_{geo}$ is the CT scanner's geometrical modulation transfer function f is spatial frequency and $f_c$ is the scanner's cutoff frequency. $MTF_{geo}$ depends on focal spot size, a detector width and the scanner's geometry. It can be calculated for convention focal spots and detectors from the equation $$MTF_{geo}(f) = \text{sinc}(\pi \cdot f \cdot a(M-1)/M) \cdot \text{sinc}(\pi \cdot f \cdot w/M) \quad (10)$$

where sinc $x = (\sin x)/x$ and f, a, M and w are as defined previously. For the derivation and further discussion of Eqn (9) reference is made to Wagner et al, "The Application of Information Theory to the Assessment of Computed Tomography", Medical Physics, Volume 6, 1979, pp. 83-94.

The integral in Eqn. (9) has been defined as the information band width integral (IBWI), or $$IBWI = \int_0^{f_c} MTF_{geo}^2(f) \cdot df \quad (11)$$

As one would expect for a given cutoff frequency, the CT scanner with the greatest IBWI will produce superior images or images having a greater signal-to-noise ratio assuming all else equal.

Due to electronic, mechanical and other sources of noise, the noise equivalent number of quanta comprising the reconstructed image will be less than the detected number of photons. However, for well designed and adjusted scanners this difference will not vary widely from one scanner to another and one can write $$\text{Information Capacity} \sim N_{det} \cdot IBWI \quad (12)$$

for the same size patient reconstruction circles. Dividing Eqn. (12) by Eqn. (5), one obtains $$\text{Information Capacity/rad} \sim \xi_{rad} \cdot IBWI \quad (13)$$

Since it is desirable to obtain the maximum information for a given radiation absorbed dose, the right hand side of Eqn. (13) defines a Figure of Merit for CT Scanners. That is, $$\text{CT Figure of Merit} = \xi_{rad} \cdot IBWI \quad (14)$$

Table III compares the IBWI's and Figures of Merit for the three prior art CT scanners discussed above.

TABLE III

| Cutoff Frequencies, Information Bandwidth Integral (IBWI) Values and Figures of Merit for Prior Art CT Scanners | | | |
|---|---|---|---|
| Manufacturer and Unit | Cutoff Frequency, cm$^{-1}$ | IBWI cm$^{-1}$ | Figure of Merit, cm$^{-1}$ |
| Ohio Nuclear Δ-Scan 2020 | 6.2 | 2.7 | 1.4 |
| GE CT/T 8800 | 5.9 | 4.9 | 2.6 |
| EMI 7000 | 6.7 | 3.9 | 2.8 |

Eqn. (14) indicates that CT scanner performance can be improved either by increasing its dose efficiency, cutoff frequency or geometrical MTF. However, it is doubtful that with current X-ray detector technology that dose efficiencies greater than 70% are possible for an array of small detectors. As discussed previously the cutoff frequency and $MTF_{geo}$ can be improved by employing smaller or effectively smaller detector apertures in 4th generation geometries and by reducing the sampling distance, which in turn depends on detector size, in 3rd generation designs. At present, it is questionable whether detector elements smaller than 0.9 mm for gas and 1.8 mm for solid state sensitive volumes can be fabricated with sufficiently good dose efficiency. However, no such problem exists when direct geometrical magnification is employed to reduce the effective detector size.

Pertinent data for improved scanner geometries and the Multiple Beam Geometry based on the above consideration are tabulated in Table IV. The detectors employed in the 4th Generation Scanner and Multiple Beam CT Scanner according to the invention are assumed to be identical to those currently employed in the EMI 7000 Scanner. Forty-nine groups of detectors were assumed for the Multiple Beam Geometry with each group being comprised of fifteen detectors. In all cases a pixel size of 0.5 mm was assumed and the filter function cutoff frequency was taken to be equal to that of the pixel Nyquist frequency except for the 3rd Generation design where it was taken to be equal to the sampling Nyquist frequency.

TABLE IV

| Pertinent Data for Improved CT Geometries | | | | | |
|---|---|---|---|---|---|
| Focus-to-Det. Dist. (cm) | Pivot Pt. Mag. | Focal Spot (mm) | Detector Aperture (mm) | Sampling Distance (mm) | Cutoff Freq.* cm$^{-1}$ |
| 4th Generation | | | | | |

TABLE IV-continued

Pertinent Data for Improved CT Geometries

| | Focus-to-Det. Dist. (cm) | Pivot Pt. Mag. | Focal Spot (mm) | Detector Aperture (mm) | Sampling Distance (mm) | Cutoff Freq.* $cm^{-1}$ |
|---|---|---|---|---|---|---|
| (2400 detectors) | 149.9 | 2.36 | 0.6 | 1.79 | 0.78 | 10 |
| 3rd Generation (793 detectors) | 167.7 | 2.15 | 1.2 | 0.90 | 1.20 | 8.9 |
| Multiple Beam (735 detectors) | 180 | 2.73 | 0.4 | 1.79 | 0.90 | 10 |

*0.5 mm pixel size assumed

In the following Table V, the dose efficiencies, IBWI's and Geometrical Figures of Merit of the improved geometries are compared.

TABLE V

Dose Efficiencies, Information Bandwidth Integral (IBWI) Values and Figures of Merit for Improved CT Geometrical

| Geometry | Efficiency | IBWI $cm^{-1}$ | Geometrical Figure of Merit, $cm^{-1}$ |
|---|---|---|---|
| 4th Generation (2400 detectors) | 70 | 5.4 | 3.8 |
| 3rd Generation (793 detectors) | 54 | 5.7 | 3.1 |
| Multiple Beam (735 detectors) | 66* | 6.3 | 4.2 |

*5% primary beam loss is due to prepatient collimation and penumbra effects

Due to the small focal spot and large magnification of the Multiple Beam Geometry according to the invention, its IBWI, $MTF_{geo}$ and Figure of Merit is superior to that of the other proposed improved geometries which in turn are superior to those of the prior art scanners listed in Table III. The large magnification allowed with this geometry is due to the fact that a continuous ring of detectors is not required. If the Multiple Beam Geometry were to employ the same specifications as the 4th Generation Geometry listed in Table IV, its $MTF_{geo}$ would be identical.

Figure 8:
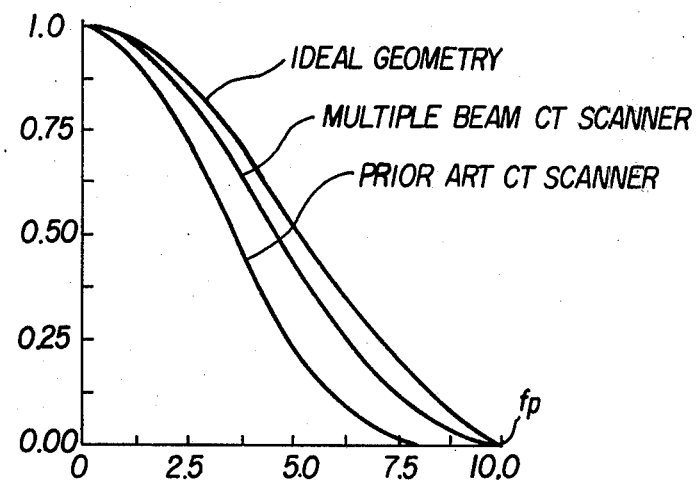
FIG. 8 is a graph illustrating the improved performance of the scanner of the invention relative to a conventional fourth generation scanner, as also compared with performance of a CT scanner having an ideal geometry.

For further analysis of the comparative performance of other prior art CT Scanners, reference is made to Barnes et al, "Optimizing Computed Tomography (CT) Scanner Geomerty", Proc. Society of Photo-Optical Instrumentation Engineers (SPIE), Volume 173, 1979, pp. 225-237. FIG. 8, the derivation of which is explained in detail in Barnes et al., supra, compares the performance of the multiple beam CT scanner according to the invention.

For a 512 by 512 matrix a minimum of $(512)^2$ or 262,144 independent samples are required in order to reconstruct the matrix. The 0.895 mm sampling distance (i.e., one-half the detector aperture width as required by sampling theory) and 2.73 magnification factor of the Multiple Beam Geometry results in 780 samples per detector for a 25.6 cm diameter patient circle. The 735 detectors obtain 573,300 samples which is more than sufficient to reconstruct a 512 by 512 matrix. A variety of mathematical algorithms have been employed to reconstruct cross-sectional images from projections, and for further analysis of reconstruction algorithms, reference is made to Brooks and DiChiro, "Principles of Computer Assisted Tomography (CAT in Radiographic and Radioisotopic Imaging", Physics in Medicine and Biology, Volume 21, 1976, pp. 689-732.

From the above discussion, it is seen that the multiple beam CT scanner geometry according to the invention allows the use of a limited number of small detectors and data acquisition electronics. Presently, the CT scanner of the invention envisions the use of 25-99 groups of detectors with each group consisting of from 10-60 detectors. In one preferred embodiment, 49 groups of detectors are employed, with each group consisting of 15 detectors. Further advantages realized by the CT scanner geometry of the invention is the enhanced resolution due to the selection of detectors having small apertures, and the improved X-ray dose efficiency achieved by the prepatient collimation in which virtually all the X-rays that penetrate the patient are detected, further resulting in low noise scans for a given patient dose. Accordingly, the improved multiple beam CT scanner geometry according to the invention results in reduced manufacturing costs while nevertheless yielding maximum information for a given patient radiation dose.

High quality AP and lateral scan or scout views can also be obtained by the design according to the invention by placing additional groups of detectors in the appropriate position for the AP and lateral scan views. In that event, the additional detectors would only be used for these views and would then require inactivation of the multiple beam defining collimator.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A multiple beam computed tomography (CT) scanner for constructing an image of a cross-sectional slice of the body of a patient, comprising:
   source means for projecting a fan-shaped beam of X-ray radiation from a focal spot towards said body;
   means for rotating said source means in a first direction around said body;
   a detector ring comprising plural interspaced groups of closely spaced detectors, each having a detector aperture for receiving X-ray radiation, arranged in a ring around said body, said detector ring and said source means arranged in a common plane intersecting said cross-sectional slice of said body;
   a radiation collimator having plural collimator apertures rotatably mounted between said source means and said patient body; and
   means for rotating said collimator in a second direction opposite said first direction in synchronism with the rotation of said source means such that the collimator apertures maintain alignment with respective detector groups during rotation of said source means,
   wherein the synchronous rotation of said source through an angle $\theta$ and said collimator through an angle $\phi$ relative to said source is governed by the transcendental equation, $$R \cdot \sin(\theta - \phi) = r \cdot \sin\phi$$

wherein r and R are the radii of circles defined by the locus of the source means focal spot and the detector ring, respectively.

2. A scanner according to claim 1, further comprising:

said detector ring comprising 25-99 groups of detectors;

wherein each detector group comprises 10-60 individual closely spaced detectors.

3. A scanner according to claim 2, wherein said detector ring comprises 49 detector groups, each group comprising 15 detectors.

4. A scanner according to claim 1, further comprising:

each detector group having a minimum dimension (L) selected in relation to the size (a) of the focal spot and the collimator position according to the following relationship:

$$L > a \cdot (D-d)/d$$

where D is the focal spot-to-detector distance and d is the focal spot-to-collimator distance, and each collimator aperture dimension (l) given by the relationship:

$$l > L \cdot d/D.$$

5. A scanner according to claim 4, further comprising:

said focal spot rotating to define the locus of a circle having the radius (r) equal to 66 cm ±10%;

said detector ring having a radius (R) equal to 105 cm ±20%;

said focal spot having a dimension (a) between 0.3 mm and 1.0 mm;

said collimator located at a distance of 40 cm ±25% from the source means focal spot; and said detector groups disposed symmetrically around said detector ring.

6. A scanner according to claim 1, wherein said collimator comprises:

a cylindrical body having said plural rectangular collimator apertures in the wall of said body.

7. A scanner according to claim 6, wherein said collimator cylindrical body is arranged to rotate about said source means focal spot.

8. A scanner according to claim 1, wherein said collimator comprises:

a tilted frustum-shaped body having said plural collimator apertures formed as slots in the wall of said body.

9. A scanner according to claim 8, wherein said collimator tilted frustum-shaped body is arranged to rotate about an axis defined by the center of the patient body.

10. A scanner according to claim 8, wherein said collimator tilted frustum-shaped body is arranged to rotate about said source means focal spot.

11. A scanner according to claims 1, 2, 3, 4, 5, 6, 7, 8, 9 or 10, further comprising:

position detecting means for detecting the position of said source means as said source means rotates around said body, and servo tracking means coupled to said position detector means and said groups of detectors for orienting said groups of detectors in respective position to track the rotation of said source means such that radiation radiated from said source means is incident at essentially a 90° angle to the plane defined by each detector aperture at each detector aperture.

* * * * *